(12) United States Patent
Gerlach et al.

(10) Patent No.: US 7,921,852 B2
(45) Date of Patent: *Apr. 12, 2011

(54) METHOD AND DEVICE FOR FORMING CURVED SECTIONS IN A TRANSPARENT MATERIAL

(75) Inventors: Mario Gerlach, Hohen Neuendorf (DE); Carsten Lang, Eisenberg (DE); Dirk Mühlhoff, Kunitz (DE); Markus Sticker, Jena (DE); Mark Bischoff, Jena (DE); Michael Bergt, Weimar (DE)

(73) Assignee: Carl Zeiss Meditec AG, Jena (DE)

( * ) Notice: Subject to any disclaimer, the term of this patent is extended or adjusted under 35 U.S.C. 154(b) by 1451 days.

This patent is subject to a terminal disclaimer.

(21) Appl. No.: 10/565,018

(22) PCT Filed: Jul. 13, 2004

(86) PCT No.: PCT/EP2004/007734
§ 371 (c)(1),
(2), (4) Date: Jan. 18, 2006

(87) PCT Pub. No.: WO2005/011545
PCT Pub. Date: Feb. 10, 2005

(65) Prior Publication Data
US 2006/0195075 A1 Aug. 31, 2006

(30) Foreign Application Priority Data
Jul. 18, 2003 (DE) ................... 103 32 815

(51) Int. Cl.
*A61B 19/00* (2006.01)
*A61B 18/20* (2006.01)
(52) U.S. Cl. .......................................... 128/898; 606/4

(58) Field of Classification Search .................. 606/4–6, 606/10–12; 607/88–92; 128/898
See application file for complete search history.

(56) References Cited

U.S. PATENT DOCUMENTS

| 4,901,718 | A |   | 2/1990  | Bille et al. |        |
|-----------|---|---|---------|--------------|--------|
| 5,549,632 | A |   | 8/1996  | Lai          |        |
| 5,984,916 | A | * | 11/1999 | Lai          | 606/11 |
| 5,993,438 | A | * | 11/1999 | Juhasz et al.| 606/5  |

(Continued)

FOREIGN PATENT DOCUMENTS

DE 101 24 358 C1 10/2002

(Continued)

OTHER PUBLICATIONS

Application and File History of U.S. Appl. No. 10/566,009, Inventors Dirk Muehlhoff et al., filed Jan. 25, 2006.

*Primary Examiner* — Ahmed M Farah
(74) *Attorney, Agent, or Firm* — Patterson Thuente Christensen Pedersen, P.A.

(57) ABSTRACT

The invention relates to a method for forming curved sections in a transparent material, especially in a cornea, by producing optical breaks at various points in the material by means of pulsed laser beams focused into the material. The laser beam is deviated in a two-dimensional manner from a deviation point in order to form the section by arranging the optical breaks in a sequence. The two-dimensional deviation occurs such that the areas of the optical opening along a curve, whereon the optical openings are arranged in a sequence, are arranged at a distance in relation to the deviation point according to an angle function which is not linear and which is adapted to the curvature of the section. The areas along the curve adjacent to optical openings inside a specific tolerance range are arranged at an even distance.

17 Claims, 4 Drawing Sheets

U.S. PATENT DOCUMENTS

| | | |
|---|---|---|
| 6,110,166 A | 8/2000 | Juhasz |
| 6,325,792 B1 | 12/2001 | Swinger et al. |
| 6,497,701 B2 | 12/2002 | Shimmick et al. |
| 6,608,674 B2 | 8/2003 | Gerlach et al. |
| 6,805,694 B2 | 10/2004 | Donitzky |
| 7,101,364 B2 | 9/2006 | Bille |
| 2001/0031960 A1 | 10/2001 | Kliewer et al. |
| 2003/0014042 A1 | 1/2003 | Juhasz et al. |
| 2003/0105457 A1 | 6/2003 | Mrochen et al. |

FOREIGN PATENT DOCUMENTS

| | | |
|---|---|---|
| DE | 103 23 422 A1 | 4/2004 |
| WO | WO 93/16631 | 9/1993 |
| WO | WO 94/09849 | 5/1994 |
| WO | WO 97/30752 | 8/1997 |
| WO | WO 98/14244 | 4/1998 |
| WO | WO 01/67978 A1 | 9/2001 |
| WO | WO 01/85075 A1 | 11/2001 |
| WO | WO 02/32353 A2 | 4/2002 |

* cited by examiner

METHOD AND DEVICE FOR FORMING CURVED SECTIONS IN A TRANSPARENT MATERIAL

FIELD OF THE INVENTION

The invention relates to a method of producing curved cuts in a transparent material, in particular in the cornea of the eye, by generating optical breakthroughs at different locations in the material by means of pulsed laser radiation focused into the material, wherein said laser radiation is two-dimensionally deflected so as to produce the cut by a series of optical breakthroughs. The invention further relates to an apparatus for producing curved cuts in a transparent material, in particular in the cornea of the eye, said apparatus comprising a pulsed laser radiation source which focuses laser radiation into the material and causes optical breakthroughs to form there, wherein a deflecting unit deflecting the laser radiation two-dimensionally and a control unit controlling said deflecting unit are provided so as to form the cut by sequential arrangement of the optical breakthroughs in the material.

BACKGROUND OF THE INVENTION

Curved cuts within a transparent material are generated, in particular, in laser-surgical methods, especially in ophthalmic surgery. This involves focusing treatment laser radiation within the tissue, i.e. beneath the tissue surface, so that optical breakthroughs are generated in the tissue.

In the tissue, several processes initiated by the laser radiation occur in a time sequence. If the power density of the radiation exceeds a threshold value, an optical breakthrough will result, generating a plasma bubble in the material. After the optical breakthrough has formed, said plasma bubble grows due to expanding gases. If the optical breakthrough is not maintained, the gas generated in the plasma bubble is absorbed by the surrounding material, and the bubble disappears again. However, this process takes very much longer than the forming of the bubble itself. If a plasma is generated at a material boundary, which may quite well be located within a material structure as well, material will be removed from said boundary. This is then referred to as photo ablation. In connection with a plasma bubble which separates material layers that were previously connected, one usually speaks of photo disruption. For the sake of simplicity, all such processes are summarized here by the term optical breakthrough, i.e. said term includes not only the actual optical breakthrough, but also the effects resulting therefrom in the material.

For a high accuracy of a laser surgery method, it is indispensable to guarantee high localization of the effect of the laser beams and to avoid collateral damage to adjacent tissue as far as possible. It is, therefore, common in the prior art to apply the laser radiation in a pulsed form, so that the threshold value for the power density of the laser radiation required to cause an optical breakthrough is exceeded only during the individual pulses. In this regard, U.S. Pat. No. 5,984,916 clearly shows that the spatial extension of the optical breakthrough (in this case, of the generated interaction) strongly depends on the pulse duration. Therefore, precise focusing of the laser beam in combination with very short pulses allows the placement of the optical breakthrough in a material with great point accuracy.

The use of pulsed laser radiation has recently become established practice particularly for laser-surgical correction of visual defects in ophthalmology. Visual defects of the eye often result from the fact that the refractive properties of the cornea and of the lens do not cause orderly focusing on the retina.

U.S. Pat. No. 5,984,916 mentioned above, as well as U.S. Pat. No. 6,110,166, describe methods of the above-mentioned type for producing cuts by means of suitable generation of optical breakthroughs, so that, ultimately, the refractive properties of the cornea are selectively influenced. A multitude of optical breakthroughs are joined such that a lens-shaped partial volume is isolated within the cornea of the eye. The lens-shaped partial volume which is separated from the remaining corneal tissue is then removed from the cornea through a laterally opening cut. The shape of the partial volume is selected such that, following removal, the refractive properties of the cornea are modified so as to cause the desired correction of visual defect. The cuts required here are curved, which makes three-dimensional shifting of the focus necessary. Therefore, a two-dimensional deflection of the laser radiation is usually combined with a simultaneous focus shift.

In order to isolate the partial volume, it is indispensable, of course, to generate the optical breakthroughs at predetermined locations. In doing so, the quality of the generated cut depends on the uniformity of the arrangement of the optical breakthroughs. This applies, in particular, to the aforementioned ophthalmic operations effecting a refractive correction, because here, the quality of the cut is inseparably connected with the optical quality of the result achieved.

In order to produce the curved cuts with high quality, it is therefore indispensable to arrange the optical breakthroughs in series with a high density. However, this is detrimental to quick production of a cut for two reasons: On the one hand, the time required for generating the cut increases as the required number of optical breakthroughs increases. On the other hand, a tight sequential arrangement of optical breakthroughs requires waiting after each breakthrough until the amount of gas generated in the plasma bubble has been re-absorbed by the surrounding tissue, before the next optical breakthrough can be generated immediately adjacent thereto. Otherwise, the optical breakthrough could not be generated with sufficient safety, because the laser radiation would possibly be focused into a still existing plasma bubble and would not cause an optical breakthrough there.

Therefore, it is an object of the invention to improve a method and an apparatus for producing curved cuts as mentioned above, so that a good quality of the optical cut surface is possible while at the same time forming the cut as quickly as possible.

SUMMARY OF THE INVENTION

According to the invention, this object is achieved by a method of the aforementioned type, wherein two-dimensional deflection is effected such that the locations of optical breakthroughs are spaced apart, along a curve at which the optical breakthroughs are sequentially arranged, according to a deflection-related angular function which is non-linear and adapted to the curvature of the cut such that the locations of optical breakthroughs adjacent along the curve are spaced by the same distance within a certain tolerance.

The object is further achieved by an apparatus of the aforementioned type, wherein the control unit controls the deflecting unit two-dimensionally according to a deflection function such that the locations of optical breakthroughs along a curve on which the optical breakthroughs are sequentially arranged are spaced apart according to a deflection-related angular function, which is non-linear and adapted to the curvature of the cut, such that the locations of optical breakthroughs adjacent along the curve are spaced by the same distance within a certain tolerance.

The invention assumes a projection geometry in which equidistant angular spacings of the deflection result in equidistantly located points in a plane perpendicular to the main axis of incidence. According to the invention, the use of non-equidistant angular distances ensures that, in the plane perpendicular to the main axis of incidence the point distances vary such that the curved cut surface leads to equidistant locations of the optical breakthroughs.

The invention achieves optical breakthroughs, which are adjacently located along a curve in the curved cut, and equidistantly located within precisely determined limits. The distance of thus adjacent optical breakthroughs can now be adjusted such that a minimum number of optical breakthroughs are sufficient to generate a desired curved cut. Further, the distance can be reliably adjusted such that the optical breakthroughs are joined at a frequency which is as high as possible, without the danger of trying in vain to generate an optical breakthrough in a not yet collapsed plasma bubble of the adjacent optical breakthrough.

The invention provides flexibility as regards the sequential arrangement of the breakthroughs. What is desired for the approach according to the invention is merely that the breakthroughs adjacently arranged in a sequence satisfy the above-mentioned geometric conditions, whereby the curve can be linked with the time sequence in which the breakthroughs were generated and may, in particular, correspond to it.

At the same time, the invention enables working with biaxial deflection of the laser radiation generating the optical breakthroughs. This is usually very easy to perform. A complex two-dimensional displacement having no deflection about fixed axes, which could be achieved, for example, by two-dimensional displacement of an end of a light guide, is not required by the approach according to the invention.

A two-dimensional deflection in the sense of the invention includes any deflection which deflects the laser radiation in two directions. Conventionally, a deflection about two orthogonal axes is effected by means of tilting mirrors. In doing so, the axes are naturally located some distance from and perpendicular to the main axis of incidence of the radiation on the object (e.g. the eye). Projection of the axis of the deflection effected first along the main axis of incidence onto the axis of the subsequent deflection yields a basis for the two-dimensional deflection. Thus, in general, the axes need not intersect; they need not be orthogonal either in the aforementioned projection; for example, a deflection according to polar coordinates, which can be realized by the use of a tumbling mirror or of a rotary prism scanner, is also possible.

In any case, it is always possible to indicate two bases defining a plane perpendicular to the main axis of incidence, to which bases the angular function is related. The angular function is naturally adapted to the curvature of the cut surface function. It is related to the two-dimensional deflection, indicates the location of an optical breakthrough relative to the deflection (point of deflection, bases of the deflection) and is, therefore, generally also two-dimensional. Depending on the type of deflection, this angular function may be separable into two one-dimensional angular functions. In the case of a biaxial deflection, for example, a separate angular function can be indicated for each axis, said function defining the angle between the axis of deflection and a straight line from the crossing point of central beam axis-axis of deflection up to the location of the optical breakthrough. The crossing point may be regarded as the point of deflection for the deflection about the respective axis of deflection. Thus, a person skilled in the art can obtain a predetermined value for the angular function to be used, for example, by connecting locations, which are equidistantly located in the curved cut to the point of deflection.

The invention allows placement of the locations of the optical breakthroughs that are adjacent to each other along a curve with a precisely determined distance from each other by deflection of the laser beam. Since the cut is generated by two-dimensional deflection and the optical breakthroughs usually generate plasma bubbles having a generally spherical volume, the distance between randomly adjacent locations of the optical breakthroughs in the cut depends on the arrangement of the optical breakthroughs in the cut, which arrangement may be regarded, in simple approximation, as a planar lattice structure. The distance of a certain optical breakthrough from its neighbor varies according to the lattice structure. Due to this variation, it is not always required to precisely set the same distance between the locations along the curve. Rather, it is sufficient to keep the distance constant within certain tolerances.

In order to fill the cut surface completely with the spherical plasma bubbles, it is convenient to select a distance for the locations of the optical breakthroughs in the cut exceeding the minimum distance in the lattice structure. The tolerances will advantageously be selected lower than the geometry-dependent variation of the distances between the locations of directly adjacent optical breakthroughs. A tolerance of 20% has turned out to be favorable.

As already mentioned above, the optical breakthroughs are generated by the use of pulsed laser radiation. Thus, the optical breakthroughs are generated, certain step widths apart, by deflection. The step width, i.e. the angular distances of the optical breakthroughs, is/are equally influenced by the deflection function, according to which deflection is effected, and by the time interval between two subsequent pulses, i.e. the pulse rate. Both of these parameters are thus suitable for adjusting the angular function according to the invention, and keeping one constant while varying the other is possible as well as a simultaneous variation of the pulse repetition rate and the deflection function.

A constant pulse repetition rate has turned out to be particularly easy to realize when providing the laser radiation. Therefore, in a further embodiment, it is preferred to provide the laser radiation in a uniformly pulsed manner and to effect deflection according to a deflection function, which is non-linear in at least one direction, i.e. to design it such that the speed of adjustment of the two-dimensional deflection depends on the present angle of deflection, in order to realize the angular function according to the invention. This applies, in particular, to the case of a deflection about two mutually perpendicular axes, which can be realized by particularly simple means.

With such a deflection, it is possible, in particular, to guide the laser radiation in a meander-shaped pattern over the region in which the cut is to be produced. In doing so, the laser beam is ideally deflected back and forth in parallel lines and a change of the deflection about the other axis is effected perpendicular thereto, at the end of a respective line so as to achieve a line feed. Depending on the design of the cut, the lines are, of course, not the same length. Further, so as to take the curvature of the cut into account and to achieve the non-linear angular function according to the invention, said lines are usually not equidistant to each other either; their distance varies according to the position of the line on the cut. With certain cut shapes it may also occur that the deflection has to be adjusted for displacement of the lines while proceding on a line, in order to obtain the angular function adapted to the curved cut.

In order to achieve the desired curvature of the cut, a corresponding shift of the focusing has to be ensured, of course, during two-dimensional deflection. However, the procedure and means required for this purpose are known to the skilled person from the prior art, so that they need not be discussed here any further. It should suffice here to note that the adjustment of the focus according to the curved cut to be achieved is suitably synchronized with the two-dimensional deflection so that each deflection has a focus position associated therewith.

In most cases, ophthalmic operations require approximately spherical cuts or spherically curved cuts with a cylindrical component, because the cornea of the eye is approximately spherically curved. For such cuts, in particular, in the case of uniformly pulsed laser radiation, a deflection is advantageous wherein the speed of deflection change at the periphery of the region of the cut is smaller than at the center so as to consider for the increasing inclination of the cut surface at the periphery of said region relative to the plane of the two-dimensional deflection.

In spherically curved cuts, exact adjustment of the step width appearing between two adjacent breakthroughs in a plane parallel to the two-dimensional deflection is particularly easy. In this respect, a further embodiment for cuts curved with a radius R is preferred, wherein the laser radiation is incident in the material along a main axis of incidence and is deflected in a plane perpendicular to said main axis of incidence in a biaxial manner along an x-axis and a y-axis, wherein a step width dx between locations on the curve of adjacent optical breakthroughs is adjusted in the plane in x-direction, for which step width the following applies:

$$dx = D \cdot \frac{R1}{\sqrt{R1^2 - x^2}},$$

wherein D designates the distance of the optical breakthroughs (8) and $$R1 = R \cdot \cos\left(\arctan\frac{y}{R}\right).$$

Analogously, the pulse rate of the laser radiation can be chosen such that it is higher at the periphery of the region of the cut than at the center thereof.

The described meander-shaped pattern is a special case of a two-dimensional deflection having two deflection functions which are assigned to one of the coordinates of the two-dimensional deflection, wherein one of the two deflection functions is parametrized with the coordinate to which the other of the two deflection functions is assigned. Such an embodiment of the invention allows the use of substantially separated deflection functions and avoids the complexity of two-dimensional deflection functions, which are, of course, possible per se, but are much more difficult to handle in terms of data processing.

The apparatus according to the invention serves to realize the method according to the invention and comprises an accordingly designed control unit, which can be realized, for example, by a suitably programmed computer and which controls the deflecting unit as well as other components of the apparatus (e.g. focus adjustment). A particularly convenient realization of the projection of the laser radiation into the material is a corrected F-Theta optical system, which, in a deflection from a point of deflection, leads to a uniform course of the deflection parallel to the plane of the two-dimensional deflection if the deflection is linearly controlled.

BRIEF DESCRIPTION OF THE DRAWINGS

The invention will be explained in more detail below, by way of example and with reference to the Figures, wherein.

DETAILED DESCRIPTION OF THE INVENTION

Figure 1:
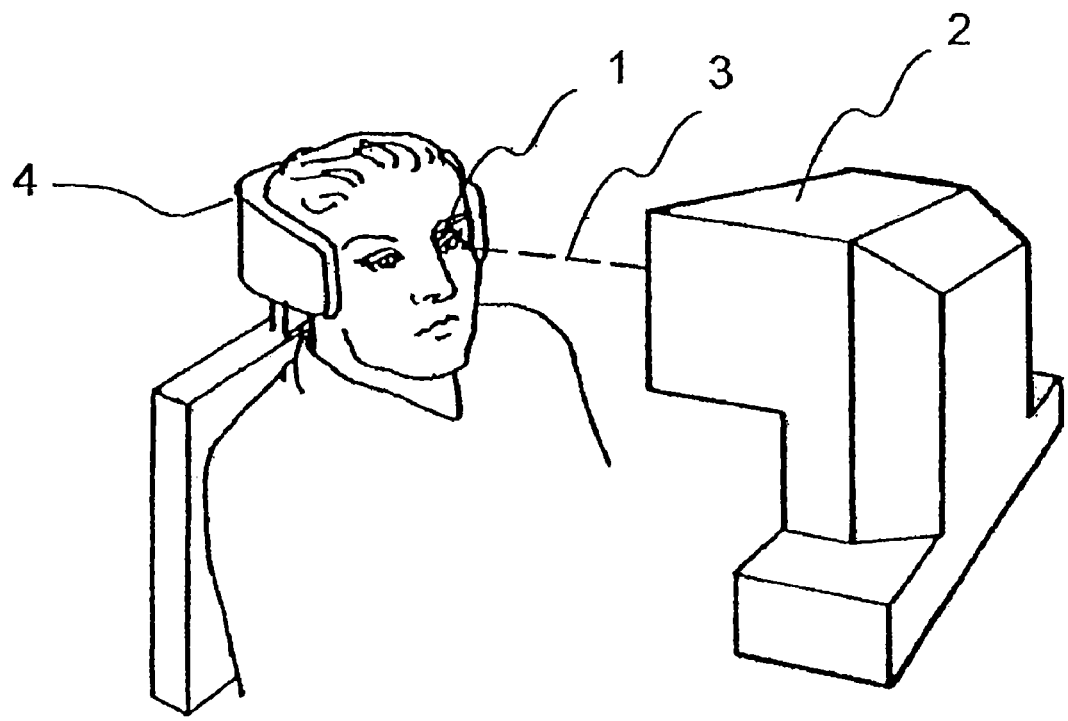
FIG. 1 is a perspective view of a patient during a laser-surgical treatment with a laser-surgical instrument.

FIG. 1 shows a laser-surgical instrument for treatment of an eye 1 of a patient, said laser -surgical instrument 2 serving to effect a refractive correction. For this purpose, the instrument 2 emits a treatment laser beam 3 onto the eye of the patient 1 whose head is immobilized in a head holder 4. The laser-surgical instrument 2 is capable of generating a pulsed laser beam 2 allowing the method described in U.S. Pat. No. 6,110, 166 to be carried out.

Figure 2:
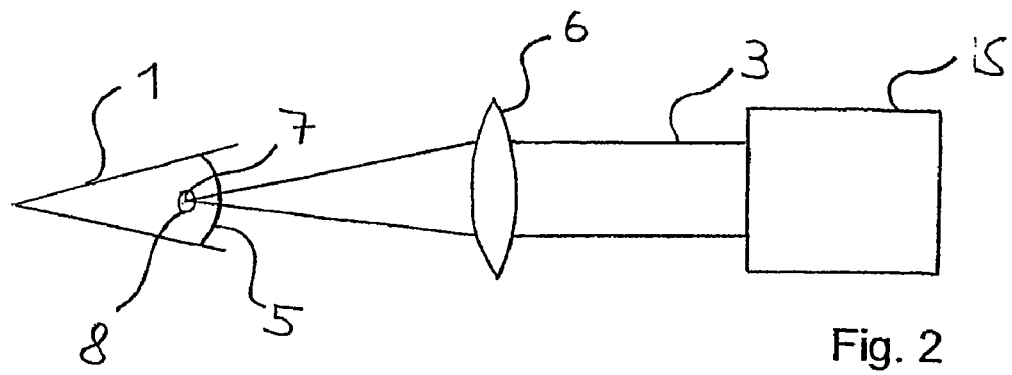
FIG. 2 depicts the focusing of a ray bundle onto the eye of the patient with the instrument of FIG. 1.

For this purpose, as schematically shown in FIG. 2, the laser-surgical instrument 2 comprises a radiation source S whose radiation is focused into the cornea 5 of the eye 1. A visual defect in the eye 1 of the patient is remedied using the laser-surgical instrument 2 to remove material from the cornea 5 such that the refractive characteristics of the cornea are modified by a desired amount. In doing so, the material is removed from the corneal stroma, which is located beneath the epithelium and Bowman's membrane, above Descemet's membrane and the endothelium.

Material removal is effected in that layers of tissue are separated in the cornea by focusing the high-energy pulsed laser beam 3 by means of focusing optics 6 in a focus 7 located in the cornea 5. Each pulse of the pulsed laser radiation 3 generates an optical breakthrough in the tissue, said breakthrough initiating a plasma bubble 8. As a result, the tissue layer separation covers a larger area than the focus 7 of the laser radiation 3. By suitable deflection of the laser beam 3, many plasma bubbles 8 are now arranged in series during treatment. The adjacent plasma bubbles 8 then form a cut 9, which circumscribes a partial volume T of the stroma, namely the material to be removed from the cornea 5.

Due to the laser radiation 3, the laser-surgical instrument 2 operates in the manner of a surgical knife which, without injuring the surface of the cornea 5, directly separates material layers within the cornea 5. If the cut is led up to the surface of the cornea 5 by generating further plasma bubbles 8, the material of the cornea 5 isolated by the cut 9 can be extracted laterally and, thus, removed.

Figure 3:
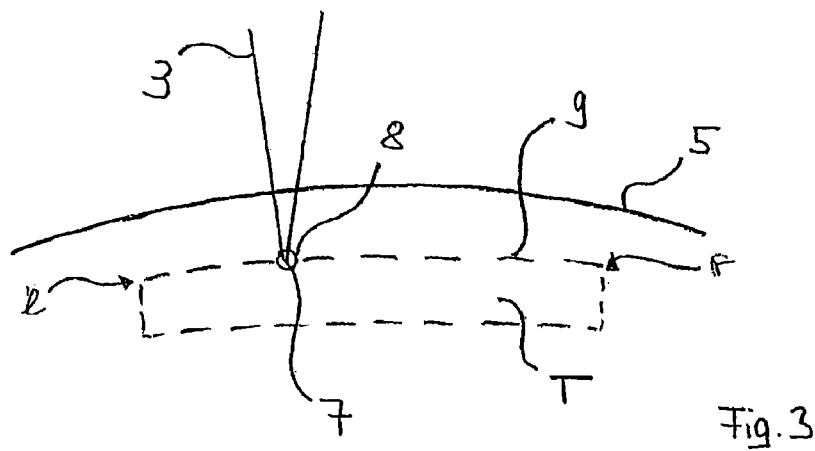
FIG. 3 is a schematic representation of a cut generated during laser-surgical treatment with the instrument of FIG. 1.

The generation of the cut 9 by means of the laser-surgical instrument 2 is schematically shown in FIG. 3. The cut 9 is formed by sequential arrangement of the plasma bubbles 8 as a result of continuous deflection of the pulsed focused laser beam 3 and of a suitable focus shift.

Figure 4:
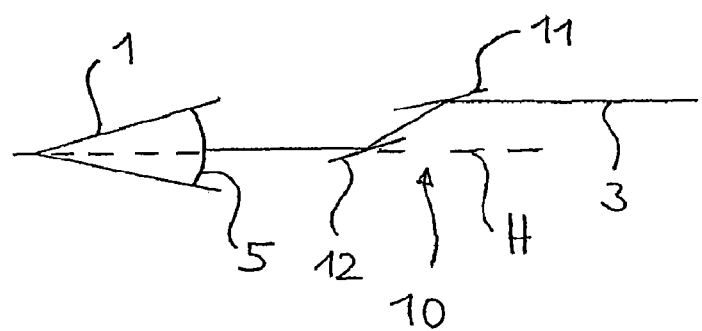
FIG. 4 depicts a deflection apparatus of the laser-surgical instrument of FIG. 1.
Figure 5:
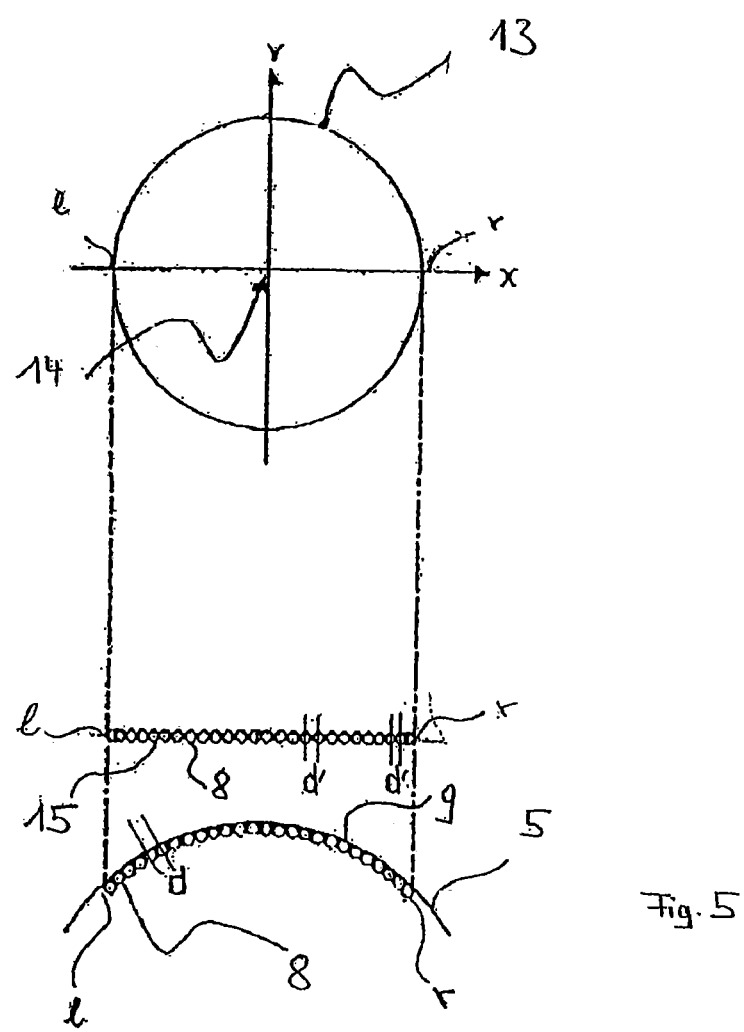
FIG. 5 depicts the arrangement of optical breakthroughs for generating a cut with the laser-surgical instrument of FIG. 1.

Deflection is effected, according to one embodiment, by means of the deflecting unit 10, schematically shown in FIG. 4, which deflects the laser beam 3 about two mutually perpendicular axes, said laser beam 3 being incident on the eye 1 on a main axis of incidence H. For this purpose, the deflecting unit 10 uses a line mirror 11 as well as an image mirror 12, thus resulting in two spatial axes of deflection which are located behind each other. The point where the main beam axis and the deflection axis cross is then the respective point of deflection. However, since the two points of deflection for the two axes of deflection are very closely spaced, relative to the distance between the deflecting unit 10 and the cornea 5, the axes of deflection can be regarded approximately as crossing in a single point of deflection. Thus, in approximation, the two axes of deflection may be considered as intersecting in the point of deflection and thus as defining a plane to which the main axis of incidence H is perpendicular. Should this approximation not be possible, the axes of deflection are to be projected into a plane perpendicular to the main axis of incidence of the beam on the cornea, in order to obtain the reference for the angular function, which shall be explained later. FIG. 5 shows a top view of the cut region 13 of a spherically curved cut to be executed in the cornea 5. The projection of the two axes of deflection which intersect at the center 14 of the cut region and are designated as x and y, respectively, is indicated on the cut region 13. The deflection by the line mirror 11 causes a displacement of the laser beam along the x-axis (i.e. a deflection about the y-axis), whereas operation of the image mirror 12 results in a displacement along the y-axis (i.e. a deflection about the x-axis).

The cut region extends from a left edge l with the coordinates $x=-x_{min}$, $y=0$, to a right edge r with the coordinates $x=x_{max}$, $y=0$. For more clarity, the edges l, r are shown in FIG. 3 again. In addition to the top view of the cut region 13, FIG. 5 bottom shows a sectional view of the cornea 5 including the cut region 13, wherein the cut is indicated along the x-axis. As can be seen, the cut 9 in the cornea 5 is generated by sequential arrangement of plasma bubbles 8 which are equidistantly spaced along the cut 9 by a distance d. The distance d depends on the diameter of the plasma bubble 8 generated by each optical breakthrough and is, for example, 3 μm.

Between the sectional view in FIG. 5, bottom, and the top view of the cut region 13 in FIG. 5, top, the sequential arrangement of the plasma bubbles 8 is represented in the form of a line 15 in a plane perpendicular to the main axis of incidence of the axes of deflection. The main axis of incidence is defined by the beam incident on the center 14. As is evident, the distance d' of the individual plasma bubbles 8 in this plane varies; the distance d' decreases toward the edges l and r and is maximal at the center, i.e. on the main axis of incidence, with $y=0$. The decrease in the distance d' is caused by non-linear control of the line mirror 11 and is selected such that the uniform distance d between the plasma bubbles 8 is adjusted in the cut 9 of the cornea 5.

With respect to the point of deflection, the locations of the disruption bubbles are consequently arranged according to a non-linear angular function. The angular function in x-direction is selected such that in the cut 9 the plasma bubbles 8 are equidistantly located despite the curvature of the cut 9. The distance d' varying as a consequence of the angular function along the (straight) line 15 thus causes a sort of pre-distortion of the distances which, together with the curvature of the cut 9, achieves the constant distance d of the locations of the plasma bubbles 8, which have been written along the line.

In order to perform a spherically curved cut with a radius R, the locations in the linear line are spaced apart, as a function of x, by d'=dx as follows:

$$dx = D \cdot \frac{R1}{\sqrt{R1^2 - x^2}},$$

wherein D designates the distance of the optical breakthroughs (8) and $$R1 = R \cdot \cos\left(\arctan\frac{y}{R}\right).$$

Figure 6:
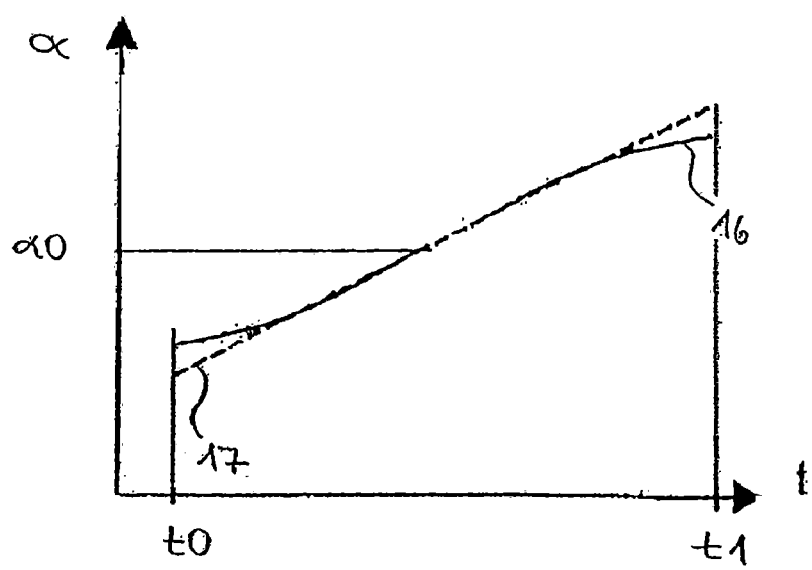
FIG. 6 is a graph illustrating the line deflection in the deflection function of FIG. 4.

The control of the line mirror 11 required for line 15 is indicated as a time sequence in FIG. 6. The time sequence of FIG. 6 shows the course of the angle of deflection α as a time-dependent line function 16 when writing the line 15, i.e. when generating the plasma bubbles 8, for the coordinate $y=0$. FIG. 6 shows the line deflection angle α, which is identical with the line coordinate x due to the uniformly pulsed emitting radiation source S and the F-theta correction of the optics. In the case of non-uniformly pulsed laser radiation, this no longer holds true, so that, in order to generalize the representation, in FIG. 6 the ultimately decisive line deflection angle α is plotted. In order to clarify that the line function 16 is non-linear, the linear course 17 is additionally plotted in FIG. 6, although it is not used to control the line mirror 11.

As FIG. 6 shows, the line mirror 11 is controlled between two time points t0 and t1 according to a line function 16, which is located symmetrically around an average value α0 and deviates from a linear function 17. At the time point t0, the line mirror 11 is positioned such that the laser beam 3 is incident on the left edge l. At the time point t1, the deflected laser beam 3 is located at the right edge r. The value α0 corresponds to the center of the cut region 13, i.e. the coordinate $x=0$. As a result of the line function 16 flattening out toward the edge, the line mirror 11 moves at a lower speed at the edge of the cut region 13, so that the plasma bubbles 8 move closer together, i.e. the distance d' decreases toward the edges l and r. Due to the curvature of the cut 9 it is thus achieved, on the whole, that the distance d of the plasma bubbles 8 in the cornea 5 is constant.

Figure 7:
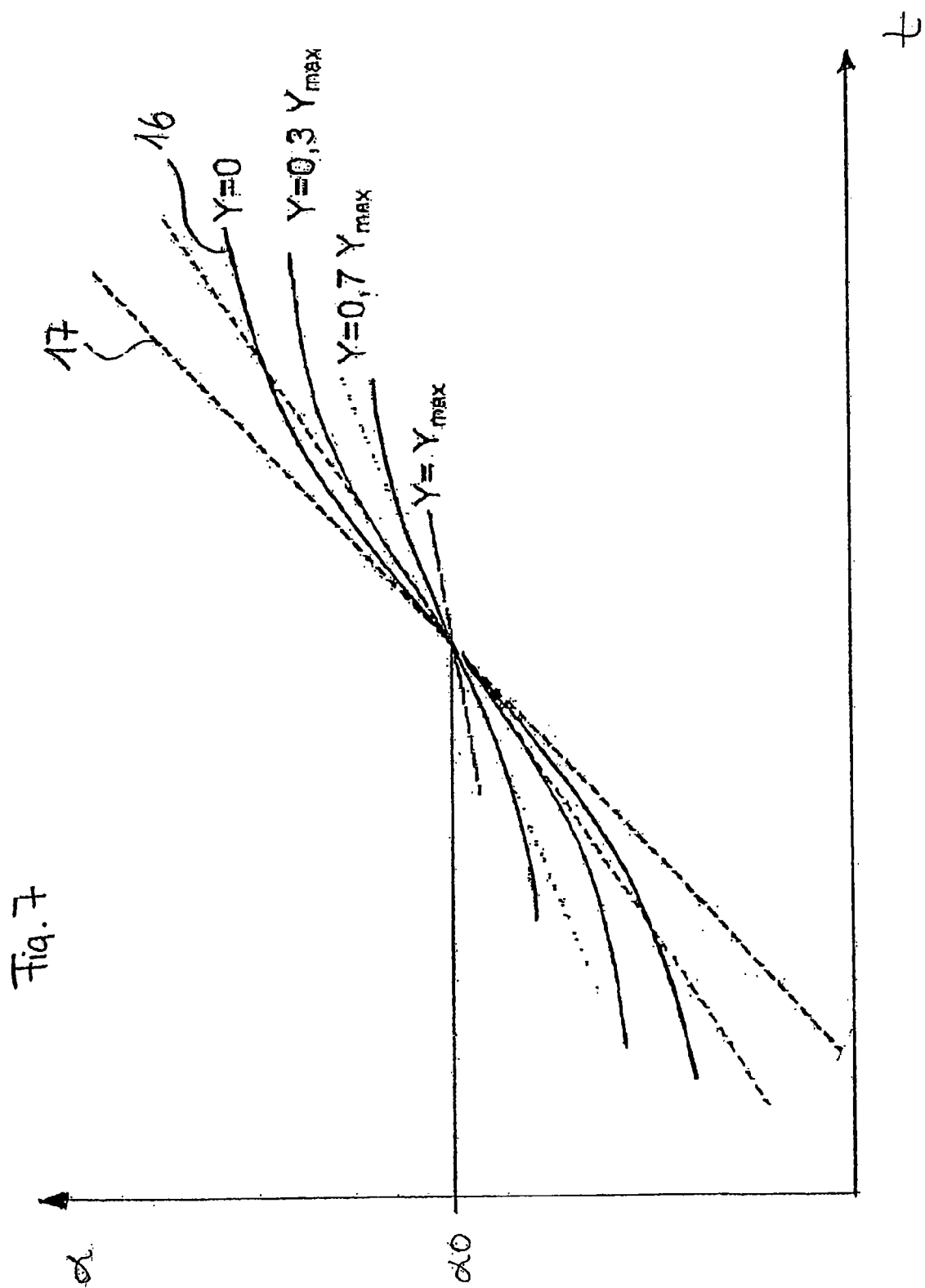
FIG. 7 is a graph of the control of the deflection apparatus of FIG. 4.

The line 15 of FIG. 5 as well as the line function 16 are represented in FIG. 6 for the simplified case of a deflection passing through the center 14. In order to obtain the spherical cut which, by line displacement, results in a circular cut region 13 in the top view representation of FIG. 5 the maximum deflection of the line mirror 11 has to be adapted, of course, to the actual position of the image mirror 12. As a result, the line function 16 is parametrized here with the y-value, i.e. with the position of the line mirror 12. FIG. 7 shows an example of a corresponding set of curves of line functions 16. The slope of the line function 16 decreases as the y-value increases; at the same time, the line-opening angle, i.e. the difference between the maximum and the minimum line deflection angle α, decreases. In individual cases, the design depends, of course, on the cut 9 and on the correction of the optics.

Thus, the line mirror 11 is controlled by a control function whose course depends on the position of the image mirror 12. This is made clear again in FIG. 8 which, in two time sequences, represents the course of the line deflection angle α

(which, in the embodiment example, is identical with or proportional to the x-coordinate) and of an image deflection angle β, which is identical with or proportional to the y-coordinate in the described embodiment which has a constantly pulsed radiation source S. In the time sequences shown in FIG. 8, the cut region 13 is raster-scanned from top to bottom. At the time point t0, the image mirror 13 is constantly positioned for deflection at the upper edge of the cut region 13, as shown by the image function 18. The line mirror 11, however, is non-linearly shifted over a small range. The time course of the control function and, thus, of the deflection angle depends on the curvature of the cut.

Figure 8:
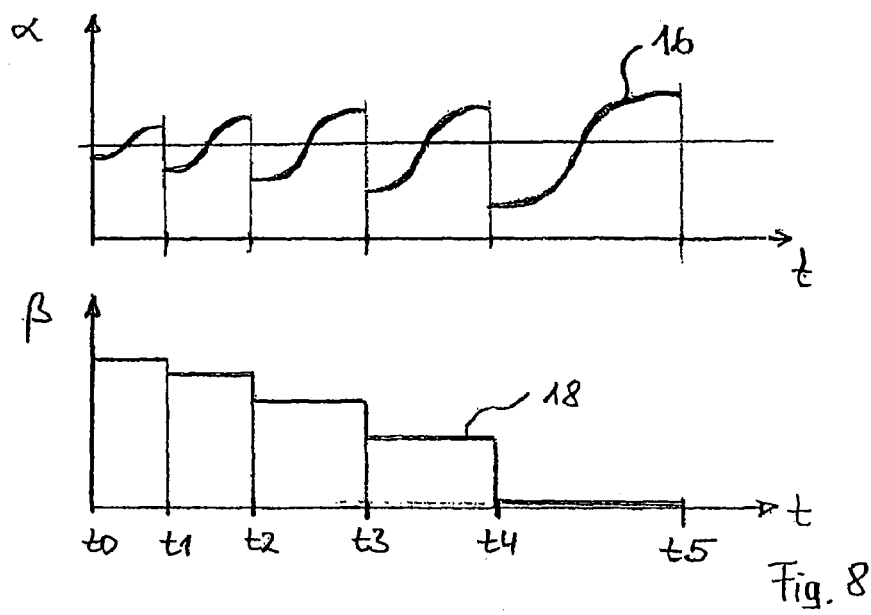
FIG. 8 depicts two time sequences of the control of the biaxial deflection according to FIG. 4.

If shifting is completed at the time point t1, the image mirror 12 moves to the next line according to the image function 18, and the line mirror in turn performs a non-linear line movement, being first returned to the left edge of the cut region 13. The deflection then caused by means of the line mirror 18 is also effected in a non-linear manner, but over a line opening angle which is increased over the previous deflection. Once the deflection along the second line is complete, the image mirror is placed in the third line at the time point t2, the angle modification caused thereby being greater than in the previous lines, because adjacent lines are not angularly equidistant. This procedure is shown in FIG. 8 up to line 15 of FIG. 5, although FIG. 8 only contains 5 lines for great simplification.

Instead of the return of the line mirror 11, the lines may also be arranged in a meander-shaped series, in which case the line function 16 is then inverted between the sections t1 and t2 as well as t3 and t4.

The invention claimed is:

1. A method of producing curved cuts in a transparent material, by generating optical breakthroughs at different locations within the material by application of pulsed laser radiation focused into the material beneath a surface of the material, wherein said laser radiation is two-dimensionally deflected in a scan pattern to produce the cut by sequential arrangement of the optical breakthroughs, comprising the steps of:
   effecting the two-dimensional deflection in the scan pattern such that the locations of optical breakthroughs are spaced apart, along a curve along which the optical breakthroughs are sequentially arranged, according to a deflection-related angular function which is non-linear and adapted to the curvature of a desired cut such that the locations of adjacent optical breakthroughs along the curve are spaced apart by substantially the same distance within a tolerance.

2. The method as claimed in claim 1, wherein the tolerance is about twenty percent.

3. The method as claimed in claim 1, further comprising:
   uniformly pulsing the laser radiation; and
   wherein the two dimensional deflection of the laser radiation in both dimensions is effected in a non-linear manner.

4. The method as claimed in claim 3, wherein the deflection is effected about two mutually perpendicular axes, and further comprising the step of guiding the laser radiation along a meander-shaped pattern.

5. The method as claimed in claim 1, further comprising deflecting the laser radiation at a lower speed, in one dimension, at the periphery of a region in which the cut is produced, than at the center of the region.

6. The method as claimed in claim 1, further comprising altering a pulse rate of the laser, at the periphery of a region in which the cut is produced such that the pulse rate of the laser radiation is higher than the pulse rate at the center of the cut.

7. The method as claimed in claim 1, wherein the two-dimensional deflection is effected according to two deflection functions associated with the two-dimensional deflection, wherein one of said two deflection functions is parameterized with the coordinate to which the other of said two deflection functions is assigned.

8. A method of producing curved cuts in a transparent material, by generating optical breakthroughs at different locations within the material by application of pulsed laser radiation focused into the material beneath a surface of the material, wherein said laser radiation is two-dimensionally deflected in a scan pattern to produce the cut by sequential arrangement of the optical breakthroughs, comprising the steps of: effecting the two-dimensional deflection in the scan pattern such that the locations of optical breakthroughs are spaced apart, along a curve along which the optical breakthroughs are sequentially arranged, according to a deflection-related angular function which is non-linear and adapted to the curvature of a desired cut such that the locations of adjacent optical breakthroughs along the curve are spaced apart by substantially the same distance within a tolerance, wherein the cut is substantially spherically curved with a radius R, the laser radiation is incident in the material along a main axis of incidence and is biaxially deflected along an x-axis and a y-axis in a plane perpendicular to said main axis of incidence, wherein a step width dx between locations on the curve of adjacent optical breakthroughs is set in the plane in x-direction according to:

$$dx = D \cdot \frac{R1}{\sqrt{R1^2 - x^2}},$$

wherein D designates the distance between centers of the optical breakthroughs and $$R1 = R \cdot \cos\left(\arctan\frac{y}{R}\right).$$

9. An apparatus for producing curved cuts in a transparent material, said apparatus comprising:
   a pulsed laser radiation source which focuses laser radiation into the material and causes optical breakthroughs within the material,
   a deflecting unit deflecting the laser radiation two-dimensionally;
   a control unit controlling said deflecting unit to form the cut by sequential arrangement of the optical breakthroughs in the material wherein the control unit controls the deflecting unit two-dimensionally in a scan pattern according to a deflection function such that the locations of optical breakthroughs along a curve on which the optical breakthroughs are sequentially arranged within the transparent material are spaced apart according to a deflection-related angular function, which is non-linear and adapted to the curvature of the cut, such that the locations of optical breakthroughs adjacent along the curve of the cut are spaced apart by a consistent distance within a tolerance.

10. The apparatus as claimed in claim 9, wherein the tolerance is about 20%.

11. The apparatus as claimed in claim 9, wherein the laser radiation source emits uniformly pulsed laser radiation, and the control unit controls the deflecting unit in both dimensions according to a non-linear deflection function.

12. The apparatus as claimed in claim 9, wherein the deflection is effected about two mutually perpendicular axes and wherein the control unit guides the laser radiation along a meander-shaped pattern.

13. The apparatus as claimed in claim 9, wherein the control unit controls the deflecting unit such that deflection in one dimension is effected at a lower speed at a periphery of a region in which the cut is produced, than at a center of the region.

14. The apparatus as claimed in claim 9, wherein the control unit controls the deflecting unit such that at the periphery of a region in which the cut is produced, the control unit controls a pulse rate of the laser radiation differently from the pulse rate at the center of the cut.

15. The apparatus as claimed in claim 9, wherein the control unit controls the deflecting unit such that at the periphery of a region in which the cut is produced, a pulse rate of the laser radiation such that the pulse rate is higher than the pulse rate at the center of the cut.

16. The apparatus as claimed in claim 9, wherein the control unit controls the deflecting unit such that the two-dimensional deflection is effected according to two deflection functions assigned to the two-dimensional deflection, wherein one of said two deflection functions is parameterized with the coordinate to which the other of said two deflection functions is assigned.

17. An apparatus for producing curved cuts in a transparent material, said apparatus comprising:
- a pulsed laser radiation source which focuses laser radiation into the material and causes optical breakthroughs within the material,
- a deflecting unit deflecting the laser radiation two-dimensionally;
- a control unit controlling said deflecting unit to form the cut by sequential arrangement of the optical breakthroughs in the material wherein the control unit controls the deflecting unit two-dimensionally in a scan pattern according to a deflection function such that the locations of optical breakthroughs along a curve on which the optical breakthroughs are sequentially arranged within the transparent material are spaced apart according to a deflection-related angular function, which is non-linear and adapted to the curvature of the cut, such that the locations of optical breakthroughs adjacent along the curve of the cut are spaced apart by a consistent distance within a tolerance, wherein the control unit controls the deflecting unit such that the cut is substantially spherically curved with a radius R, the laser radiation is incident in the material along a main axis of incidence and the deflecting unit biaxially deflects the laser radiation along an x-axis and a y-axis in a plane perpendicular to said main axis of incidence, wherein the control unit sets a step width dx between locations on the curve of adjacent optical breakthroughs in the plane in x-direction according to:

$$dx = D \cdot \frac{R1}{\sqrt{R1^2 - x^2}},$$

wherein D designates the distance between centers of the optical breakthroughs and $$R1 = R \cdot \cos\left(\arctan\frac{y}{R}\right).$$

* * * * *